United States Patent [19]
Mannick et al.

[11] Patent Number: 4,925,920
[45] Date of Patent: May 15, 1990

[54] IMMUNOSUPPRESSIVE POLYPEPTIDES

[75] Inventors: John A. Mannick, Weston; Mary Rodrick, Beverly; Richard Nimberg, Sharon, all of Mass.

[73] Assignee: Brigham and Women's Hospital, Boston, Mass.

[21] Appl. No.: 55,296

[22] Filed: May 29, 1987

[51] Int. Cl.$^5$ .................. A61K 35/14; C07C 103/52
[52] U.S. Cl. ................................ 530/387; 530/326; 530/344; 530/388
[58] Field of Search ............... 530/387, 388, 344, 326; 514/21

[56] References Cited

U.S. PATENT DOCUMENTS 4,719,107  1/1988  Carosella et al. ............... 514/21

OTHER PUBLICATIONS

Glasgow et al., "Association of Anergy with an Immunosuppressive Peptide Fraction in the Serum of Patients with Cancer", N. Eng. J. Med., 291 (24), pp. 1263–1267.
Edgington et al., "A Linkage between the Hemostatic and Immune System embodied in the Fibrinolytic Release of Lymphoryte Suppressive Peptides", J. Immunol., vol. 134, No. 1, 1985, pp. 471–477.
Constantian, M. B., "Association of Species with an Immunosuppressive Polypeptide in the Serum of Burn Patients", Ann. Surg., 188 (2), pp. 209–215, 1978.
Wang et al., "Suppression of Tumor-Specific Cell-Midiated Cytotoxicity by Immunoregulatory, Alpha-Globulin like Peptides from Cancer Patients", Cancer Res., 37 (9), pp. 3022–3025, 1977.
Loda et al., "Induction of Hepatic Protein Synthesis by a Peptide in Blood Plasma of Patients with Sepsis and Trauma", Surgery, 96 (2), pp. 204–213, 1984.
Constantian et al., "An Immunosuppressive Peptide Fraction in Cancer Serum", Fed. Proc. 33 (3 part 1), p. 770, 1974.
Nimberg et al., "Isolation of an Immunosuppressor Peptide from the Ascitic Fluid of Cancer Patients", Fed. Proc. 35 (7), 1695.
Nimberg et al., "Isolation of an Immunosuppressive Peptide Fraction from the Serum of Cancer Patients", Fed. Proc. 33 (5 part 2), p. 1562, 1974.
Mowbray, J. F., *Immunology* 6:217 (1963).
Occhino, J. C., et al., *J. Immunol.* 110:685 (1973).
Nimberg, R. B., et al., *Cancer Res.* 35:148E (1975).
Constantian, M. B. et al., *Ann. Surg.* 185:75 (1977).
Miller, F., *Transplantation* 21:179 (1976).
Hakim, A. A., *J. Trauma* 17:908 (1977).
McLoughlin, G. A. et al., *Ann. Surg.* 190:297 (1979).
McIrvine, A. J. et al., *Br. J. Surg.* 70:558 (1983).
Webb, D. R. et al., *J. Immunol.* 135:3238 (1985).
Oskan, A. N. et al., *J. Clin. Immunol.* 5:172 (1985).
Ninnemann, J. L. et al., *J. Trauma* 25:113 (1985).
Munster, A. M., The Lancet 1329 (Jun. 19, 1976).
Wang, B. S. et al., *Clin. Immunol. Immunopathol.* 24:161 (1962).
Kato, K. et al., *J. Immunol.* 133:2025 (1984).
Terman, D. S. et al., *J. Immunol.* 117: 1971–1975 (1976).
Ozkan, A. N. et al., *Fed. Proc.* 44: 1267 (Abstr. 5010) (1985).
Constantian, J. D. et al., *Ann. Surg.* 185: 73–79 (1977).
Nimberg, R. B. et al., *Biochem J.* 125: 80P (1971).
Mannick, J. A. et al., *Transplantation* 5: 1231–1238 (1967).
Cooperband, S. R. et al., *Science* 159: 1243–1244 (1968).
Cooperband, S. R. et al., *Transplant. Proc.* 1: 516–523 (1969).
Glasgow, A. H. et al., *Surgery* 76: 35–42 (1974).
Bondevik, H. et al., *Surg. Forum* 18: 237–238 (1967).
Ninnemann, J. L. et al., *Immunol. Lett.* 10: 63–69 (1985).
Nimberg, R. B. et al., *J. Biol. Chem.* 247: 5056–5061 (1972).

(List continued on next page.)

*Primary Examiner*—Lester L. Lee
*Assistant Examiner*—Abdel A. Mohamed
*Attorney, Agent, or Firm*—Saidman, Sterne, Kessler & Goldstein

[57] ABSTRACT

Immunosuppressive polypeptide (ISP) in substantially pure form is disclosed. Monoclonal antibodies to ISP are also described. Treatment of immune dysfunctions with ISP in substantially pure form and anti-ISP antibodies is also disclosed.

11 Claims, 1 Drawing Sheet

OTHER PUBLICATIONS

Nimberg, R. B. et al., *Cancer Res.* 35: 1489–1494 (1975).
Glasgow, A. H. et al., *Surg. Forum.* 22: 273–275 (1971).
Cooperband, S. R. et al., *J. Immunol.* 109: 154–163 (1972).
Glasgow, A. H. et al., *Proc. Soc. Exp. Biol. & Med.* 138: 753–757 (1971).
Menzoian, J. O. et al., *Transplantation* 18: 391–394 (1974).
Menzoian, J. O. et al., *J. Immunol.* 113: 266–273 (1974).
Occhino, J. C. et al., *Fed. Proc.* 30: Abs 1491 (1971).
Constantian, M. B. et al., *Feb. Proc.* 30: Abs 3172 (1971).
McLoughlin, G. A. et al., *Ann. Surg.* 190: 297–304 (1979).
Constantian, M. B. et al., *Fed. Proc.* 34: Abs 4562 (1975).
Menzoian, J. O. et al., *Eur. Surg. Res.* 5 (Suppl. 2):34 (1973).
Mowbray, J. F. et al., *Immunology 6: 217 (1963).*
Cooperband et al., *Mitogens in Immunology,* Oppenheim and Rosenstreich (eds), pp. 555–572 (1976).
Mowbray, J. F. et al., *Transplantation* 1: 15–20 (1963).

IMMUNOSUPPRESSIVE POLYPEPTIDES

BACKGROUND OF THE INVENTION

1. Field of the Invention

The present invention relates to a substantially purified immunosuppressive polypeptide (ISP), a process of preparing the same and uses therefor.

2. Brief Description of the Background Art

Despite the many advances in the care of critically injured patients, such as modern intensive care, resuscitation, and anesthetic techniques and an increasing arsenal of powerful antibiotics, death from overwhelming sepsis and multisystem organ failure remains a problem. In these patients host-defenses have become deficient and are no longer able to recognize and eradicate invasive organisms.

The first barrier to invasion by microorganisms is the epithelium of the skin, respiratory tract, and gastrointestinal tract. If this barrier is penetrated, then both specific and non-specific means of destroying microbial invaders are brought into play. Non-specific defense mechanisms include polymorphonuclear (PMN) and mononuclear phagocytes, natural killer cells (NK), products of complement activation, and certain acute phase proteins, particularly C-reactive protein. Specific defense mechanisms include antibody formation by B-lymphocytes, direct microbial killing by T lymphocytes, and T lymphocyte activation of mononuclear phagocytes. Many abnormalities of both the specific and non-specific host-defensive mechanisms have been described in critically injured patients, including burn patients.

Increased circulating suppressor cell activity has been described in burn and trauma patients and in appropriate animal models. McIrvine, Ann. Surg., 196: 297 (1982); Munster, Lancet, 1: 1329 (1976); Miller, et al., J. Clin. Invest., 63: 202 (1979); Wang, et al., J. Clin. Invest., 66: 200 (1980); Ninnemann, et al., J. Clin. Invest., 3: 142 (1983); Wang, et al., Clin. Immunol. Immunopathol., 24: 161 (1982). The transfer of decreased resistance to infection to normal mice by splenic cells from syngeneic burned mice has been reported. Kupper, et al., J. Surg. Res., 38: 606 (1985). Suppression of lymphocyte activation by serum or serum fractions from seriously injured patients has also been repeatedly reported. Constantian, et al., Ann. Surg., 185: 73 (1977); Ninnemann, in The Immune Consequence of Thermal Injury (J. L. Ninnemann, ed.), Williams and Wilkins, Baltimore and London, 1981, pp. 66–89; Ozkan, et al., J. Clin. Immunol., 5: 172 (1985); Kato, et al., J. Immunol, 133: 2025 (1984). That serum factors play a role in the immune deficiency seen in trauma and burn patients was first suggested by the present Applicants. Constantian, et al., Ann. Surg., 185: 73 (1977). One of these serum factors, immunosuppressive polypeptide (ISP) is the subject of the present invention. The serum suppressive activity is found chiefly in low molecular weight polypeptide-containing fractions.

SUMMARY OF THE INVENTION

It is the purpose of the present invention to provide an immunosuppressive polypeptide in substantially pure form. This immunosuppressive peptide is useful in the treatment of autoimmune disease states and to abrogate graft rejection after organ transplantation. Antibodies to this polypeptide would be useful in treating the immune suppression caused by severe burns, trauma and cancer. Preferably, the antibodies used to treat the immune suppression are monoclonal antibodies. The anti-ISP antibodies of the present invention may also be used as an extracorporeal immunoadsorbent to remove ISP from individuals.

The immunosuppressive polypeptide (ISP) has been isolated and substantially purified from the serum of seriously injured patients. The ISP has a molecular weight of about 5,000. Amino acid analysis of the purified peptide has revealed the following amino acid composition:

| Amino Acid | Nmol | Moles % |
|---|---|---|
| ASP | .704 | 12 |
| THR | .177 | 3 |
| SER | .737 | 13 |
| GLU | .470 | 8 |
| PRO | .156 | 2.7 |
| GLY | 1.352 | 23 |
| ALA | .35 | 6 |
| CYS | .133 | 2.3 |
| MET | .233 | 4 |
| VOL | .170 | 3 |
| ILE | .059 | 1 |
| LEU | .113 | 2 |
| TYR | .053 | 1 |
| PHE | .110 | 2 |
| HIS | .048 | 1 |
| LYS | .174 | 3 |
| ARG | .750 | 13 |

The present invention arose out of the discovery of a biochemical purification scheme which allows, for the first time, the preparation of ISP in homogeneous pure form. The invention encompasses the ISP per se, as well as natural and pharmaceutically acceptable salts and pharmaceutically acceptable derivatives. The term "ISP" also encompasses biologically active fragments thereof. The term ISP is meant to include ISP and its precursor polypeptides, as well as biologically active fragments thereof, regardless of the source. ISP precursors are polypeptides which include the ISP amino acid sequence within a longer sequence of amino acids which precursors may or may not exhibit ISP activity in vitro. The term "ISP" includes naturally occurring as well as synthetic ISP, and active fragments and derivatives thereof.

The term "individual" is intended to include any animal, preferably a mammal, and most preferably, a human.

The invention also concerns compositions, such as diagnostic compositions, containing ISP, and methods of using these in treatment and diagnosis.

In other aspects, the invention concerns monoclonal antibodies to ISP as well as uses of polyclonal antibodies and monoclonal antibodies therapeutically and diagnostically. The invention also concerns an assay for ISP.

DESCRIPTION OF THE PREFERRED EMBODIMENTS

Figure 1:
FIG. 1 shows a PAGE gel electrophoresis of purified ISP.

An immunosuppressive polypeptide (ISP) of approximately 5000 daltons has been isolated in electrophoretically homogeneous form. ISP inhibits the activation of normal human thymus-derived lymphocytes or T-cells. It also inhibits T-cell dependent antibody formation.

Briefly, purification of ISP was achieved by the sequential use of gel filtration chromatography, high performance liquid chromatography (gel permeation), and ion exchange high performance liquid chromatography.

As used herein the term "ISP" refers to the immunosuppressive polypeptide having a molecular weight of approximately 5000 daltons, as well as biologically active fragments thereof.

As used herein the term "salts" refers to both salts of carboxy groups of the polypeptide or protein chain and to acid addition salts of amino groups of the polypeptide chain. Salts of the carboxy group may be formed with either inorganic or organic bases by means known in the art per se. Inorganic salts include, for example, sodium, calcium, ammonium, ferric or zinc salts, and the like. Salts with organic bases include those formed, for example, with amines such as triethanolamine, arginine, lysine, piperidine, caffeine, procaine and the like. Acid addition salts include, for example, salts with mineral acids such as, for example, hydrochloric acid or sulfuric acid, and salts with organic acids such as, for example, acetic acid or oxalic acid.

Derivatives may also be prepared from the functional groups which occur at side chains on the residues of the N- or C-terminal groups, by means known in the art, and are included in the invention as long as they remain diagnostically or therapeutically acceptable.

Both the salts and the derivatives encompassed by the invention are those which are therapeutically or diagnostically acceptable, i.e., those which do not destroy the biologic or immunogenic activity of ISP.

The term "PAGE" is electrophoresis as performed on a polyacrylamide gel and separates proteins or peptides on the basis of charge. If sodium dodecylsulfate (SDS) is incorporated into the gel (SDS-PAGE), the surface active nature of the SDS results in a uniform negative charge on the peptide or protein which is a function of size. The result is that separation is based on molecular size. Native PAGE denotes the employment of this technique without the presence of SDS, and thus proteins are separated on the basis of charge and size.

Under suitable circumstances, chromatographic procedures may be carried out, preferably in a narrow bore column containing a fine particle resin under increased pressure to enhance the effectiveness of separation, i.e., by high pressure liquid chromatography.

Concentration and salt removal are commonly used precursors to certain chromatographic or separation techniques employed in the invention. Salt removal may be performed by, for example, dialysis or gel filtration or by a relatively recently developed technique called control pore glass (CPG) chromatography.

A number of gel filtration and concentration techniques are also used. Certain commercial available materials are especially useful. Bio-Gel A-5m is an agarose gel filtration medium having an exclusion limit of 5,000,000 and a high resolution capacity which separates molecules on the basis of molecular weight. The Water's I-60 column is a high-performance liquid chromatography column which also separates molecules on the basis of molecular weight. Another high-performance liquid chromatography system employs a cation exchange resin which separates molecules on the basis of charge.

Salt removal is generally necessary if ion exchange or other techniques which depend on total ionic strength are employed. These preparation methods and the extent to which they are required for particular separation procedures are well known in the art.

The term "specific activity" refers to the activity of ISP in ISP assays described in this application and known in the art related to the amount of protein by weight in the sample. As specified in the current disclosure, the activity of ISP is measured according to the assay procedure set forth hereinbelow in Examples 2 and 3. An assay for ISP will be useful in order to assess and predict which individuals will experience immune suppression prior to the appearance of the severe symptoms resulting from the immune suppression. This will enable earlier treatment of the immune dysfunctions.

The techniques for detectably labelling the homogeneous ISP and the antibodies thereto of the present invention with a radiolabel, an enzyme label, or a fluorescent label are well known to those of skill in the art. Reference can be made to Chard, *An Introduction To Radioimmunoassay And Related Techniques*, North-Holland Publishing Co., Amsterdam-NY-Oxford (1978), *The Enzyme-Linked Immunoadsorbent Assay (ELISA)* by Voller, A., et al., Dynatech Europe Borough House, Rue du Pre, Guernsey, Great Britain, and *Radioiodination Techniques, Review* 18, Amersham Corporation, by A. E. Bolton, all herein incorporated by reference. Preferably, the purified ISP is labelled with $^{125}$I using the Bolton/Hunter reagent which involves succinylation of the free N-terminals and lysine.

The detectably labelled ISP and antibodies of the present invention will be useful in the immunoassay for ISP of the present invention.

"Homogeneity" is defined as the substantial absence of other proteins or peptides.

ISP is useful in the treatment of hyperimmune and autoimmune diseases as well as in the abrogation of graft rejection following organ transplant.

Anti-ISP antibodies may be prepared by techniques known to those of ordinary skill in the art. Preferably, denatured ISP will be used to elicit antibody formation. Most preferably, anti-ISP monoclonal antibodies may be prepared using the method of Mishell, B. B., et al., *Selected Methods In Cellular Immunology*, W. H. Freeman, San Francisco (1980).

The anti-ISP antibodies will be useful in the treatment of immune suppressive diseased states caused by increased levels of ISP in the individual. Administration of anti-ISP antibodies to individuals suffering from severe burns, trauma, or cancer will inhibit the immunosuppressive activity of the ISP in these individuals. Anti-ISP antobides are also useful as an extracorporeal immunoadsorbent to remove circulating ISP from an individual with elevated levels of ISP. In one embodiment the ISP antibodies may be immobilized on membranes such as collodion membranes which are adherent to activated charcoal particles. When the plasma of an individual with high levels of circulating ISP is passed over the ISP antibody-collodion-charcoal particles, the circulating ISP in the plasma will be greatly reduced.

The anti-ISP antibodies may be bound to any solid structure or particle which may be used in extracorporeal blood circulation.

Administration of the compounds useful in the method of present invention may be parenteral, intravenous, intramuscular, subcutaneous, or any other suitable means. The dosage administered may be dependent upon the age, weight, kind of concurrent treatment, if any, and nature of the immune dysfunction being treated. The effective compound useful in the method of the present invention may be employed in such forms as capsules, liquid solutions, suspensions or elixirs for oral administration, or sterile liquid forms such as solutions or suspensions. Any inert carrier is preferably used, such as saline, or phosphate-buffered saline (PBS), or any such carrier in which the compounds used in the method of the present invention have suitable solubility properties for use in the method of the present invention. Having now generally described the invention, the same may be further understood by reference to the following examples, which are not intended to be limiting unless so expressly stated.

EXAMPLE 1

Purification of ISP from serum of burn and trauma patients. Serum was collected from individual or pooled suppressive serum was obtained from burned and trauma patients. The serum was placed on a Bio-Gel A-5m (Bio-Rad Laboratories) column equilibrated with phosphate buffered saline (PBS, 0.15M NaCl, 0.01M potassium phosphate buffer, pH 7.2). The column was monitored at 280 nm and the fourth peak from the column (25,000 MW) was lyophilized and resuspended in its original volume in distilled water and applied to a 14 ml Waters I-60 high performance liquid chromatography (HPLC) column for further gel chromatography in PBS. The fourth peak from the I-60 column which appeared approximately 9.5 minutes after the start of the column run was lyophilized, resuspended in water and applied to 100 ml Bio-Gel P2 column, equilibrated in 20 mM ammonium formate (pH 6.8), for removal of residual salt. Peak 2 from the P2 column was then applied to a 14 ml Waters cation exchange HPLC column and the sample was eluted from the column with an ammonium formate gradient (pH 4.0) 10 mM to 0.5M. The first peak from the cation exchange column was then rechromatographed on the cation exchange column until the peak was homogeneous by thin-layer chromatography on silica gel. ISP activity during purification was monitored as described in the following Examples and is shown in Table 1 below.

Isolation of Serum Immunosuppressive Peptide

| Procedure | Active Fraction | % Suppression PHA | % Suppression Mishell-Dutton |
|---|---|---|---|
| Bio-Gel A-5m | pkIV (5 mg/ml) | 95 | 90 |
| Bio-Gel P2 | pk4 (100 ug/ml) | 99 | 75 |
| I-60 HPLC | pk4 (4 ug/ml) | 99 | 60 |
| Cation Exchange HPLC | pk1 (0.75 ug/ml) | 99 | 71 |

EXAMPLE 2. Measurement of ISP Activity

Preparation of PBMC

Heparinized peripheral blood was diluted 1:2 in phosphate buffered saline. PBMC were harvested by centrifugation for 35 min at $400 \times g$ on Ficoll-Hypaque. The interface cells were collected, washed three times in Minimal Essential Medium (MEM) and counted using trypan blue for viability. The cells have a viability of greater than 95%.

One hundred ul of heat inactivated serum at 25% concentration was added to $1 \times 10^5$ peripheral blood mononuclear cells (PBMC) from each of two normal donors in 100 ul of MEM complete medium. This dilution gave a final concentration of 12.5% serum and the response (expressed as cpm of 3 HTdr) to maximum and suboptimal stimulating doses of PHA and ConA was compared with the response of cultures containing 12.5% pooled normal human serum (PNHS). Serum suppressive activity was calculated by the formula:

$$\% \text{ Suppression} = 1 - \frac{(\text{cells} + \text{subject serum} + \text{mitogen}) - (\text{cells} + \text{subject serum}) \times 100}{(\text{cells} + PNHS + \text{mitogen}) - (\text{cells} + PNHS)}$$

EXAMPLE 3. Inhibition of Antibody Formation

Serum suppressive activity was also measured in a modified Mishell-Dutton assay. For this assay, splenocytes from C57B1/6 mice was suspended ($5 \times 10^5$ ml) in RPMI 1640 medium containing 10% fetal calf serum, $5 \times 10^{-5}$M 2-mercaptoethanol (2-ME), 25 mM HEPES buffer, glutamine and antibiotics. Cells ($2.5 \times 10^5$) were then added to each well of a round bottomed microtiter plate. Sheep red blood cells (SRBC) (0.025 ml of a 1% suspension; washed in PBS) were also added to each well along with control serum fractions and test serum fractions. The final volume per well was 0.2 ml. Plates were then incubated for four days at 37° C. in a 5% carbon dioxide, water saturated environment. After incubation, the cells were removed, washed twice with RPMI 1640 medium, and resuspended in 400 ul/well of complete 1640 medium. One hundred ul of cells were added to duplicate $15 \times 60$ mm Petri dishes. Four ml of 10% SRBC were added to a solution of 0.7% agarose in 1640 medium (4 ml SRBC/100 ml agarose). One ml of the agarose/SRBC suspension was added to each plate. The plates were incubated for two hours at 37° C., 1 ml of appropriately diluted guinea pig complement was added and the plates were incubated for 1 hour longer. Plaques were then counted using a dissecting microscope. All tests were performed in triplicate.

Serum showing a 50% suppression in at least two determinations in both assays was used for isolation of suppressive peptides.

EXAMPLE 4. Preparation of Monoclonal Antibodies to ISP

Mice will be immunized intraperitoneally (IP) with ISP in complete Freund's adjuvant and 2 and 3 weeks later with antigen in incomplete adjuvant. The fourth and last injection will be given in PBS. The myeloma cell line NS-1 will be used for fusion and maintained in culture under conditions known and used by those of ordinary skill in the art. Spleen cells from immunized mice will be fused with NS-1 cells using autoclaved PEG-1000 at at least a 1:1 ratio of NS-1 to spleen cells. After fusion, the cells will be cultured at 100 ul/well for a 96 well plate or 500 ul per well for 24 well plate. The following day, 100 ul or 50 ul of HAT media will be added to each well. Twenty-four hours later, the media will be replaced with fresh HAT media. This procedure will be repeated every other day six times, aspirating and feeding with HAT media, until the cells are confluent. Cultures will be cloned, the clones will be transferred, cultured, and culture media tested for antibody by the ELISA assay. First, immunoglobulin production will be tested and cultures positive for Ig-clones will be tested for antibody to the purified suppressor substance (ISP) using first semi-purified material and later completely pure ISP.

EXAMPLE 5. Immunoassay of ISP

Rabbit anti-immunosuppressive antibody in appropriate dilution in 0.1M carbonate buffer (pH 9.6) will be added to ELISA plates, incubated overnight at 4° C. and washed. Active sites on the plates will then be blocked with 5% heat inactivated fetal calf serum (FCS) in PBS (pH 7.4). Samples to be tested are added in 200 ul volumes, incubated 90 minutes at room temperature, washed three times, and then alkaline phosphate conjugated rabbit anti-human serum peptide antibody in washing solution (PBS containing Tween-20) will be added to the wells. The plates are again incubated 90 minutes at room temperature and washed in the same washing solution. The substrate, PARA-nitrophenylphosphate disodium 1 mg/ml in substrate diluent (pH 9.8, 0.05M sodium carbonate buffer with 1 mM Mg $Cl_2$ is added, 200 ul/well, incubated at room temperature for 1 hour, and stopped by addition of 100 ul 1N sodium hydroxide/well). The results are read in a standard ELISA reader. Standards of serum suppressive peptide and negative controls are used in all assays. The assay can be utilized as a simple means of detecting the concentration of suppressive peptide (ISP) in the serum of trauma and burn patients and in patients with other diseases such as advanced cancer who also manifest suppressive serum.

What is claimed as new and intended to be covered by Letters Patent of the United States is:

1. Immunosuppressive polypeptide (ISP) and salts and derivatives thereof, substantially free of impurities, wherein said ISP has a molecular weight of about 5000 daltons and the following amino acid composition:

| Amino Acid | Moles % |
|---|---|
| ASP | 12 |
| THR | 3 |
| SER | 13 |

-continued

| Amino Acid | Moles % |
|---|---|
| GLU | 8 |
| PRO | 2.7 |
| GLY | 23 |
| ALA | 6 |
| CYS | 2.3 |
| MET | 4 |
| VOL | 3 |
| ILE | 1 |
| LEU | 2 |
| TYR | 1 |
| PHE | 2 |
| HIS | 1 |
| LYS | 3 |
| ARG | 13 |

2. The ISP of claim 1 which is substantially homogeneous with respect to SDS-PAGE.

3. The ISP of claim 1 in detectably labeled form.

4. A monoclonal antibody specific for the ISP of claim 1.

5. A composition comprising the ISP of claim 1 and a pharmaceutically acceptable carrier.

6. A composition comprising the monoclonal antibody of claim 4 and a pharmaceutically acceptable carrier.

7. A method of treating immune system suppression caused by burns or trauma to an individual comprising the steps of (a) binding an antibody to ISP to a solid phase, (b) contacting the plasma of said individual with said bound antibody wherein said contact is sufficient to allow interaction of the ISP in the plasma of said individual with the solid phase antibody, and (c) returning said treated plasma to the individual.

8. A method of treating immune system suppression caused by burns, comprising administrating an anti-ISP antibody to an immune suppressed individual.

9. The method of claim 8, wherein said antibody is a monoclonal antibody.

10. A method of treating immune system suppression caused by trauma, comprising administrating an anti-ISP antibody to an immune suppressed individual.

11. The method of claim 10, wherein said antibody is a monoclonal antibody.

* * * * *

UNITED STATES PATENT AND TRADEMARK OFFICE
CERTIFICATE OF CORRECTION

PATENT NO. : 4,925,920
DATED : May 15, 1990
INVENTOR(S) : Mannick et al

It is certified that error appears in the above-indentified patent and that said Letters Patent is hereby corrected as shown below:

Column 1, line 2; after the title "IMMUNOSUPPRESSIVE POLYPEPTIDES" insert the following: —STATEMENT AS TO RIGHTS TO INVENTIONS MADE UNDER FEDERALLY SPONSORED RESEARCH AND DEVELOPMENT This invention was made with government support under 7 R01 GM 35633 awarded by the National Institutes of Health. The government has certain rights in the invention—.

Signed and Sealed this

Twenty-fifth Day of January, 1994

Attest:

BRUCE LEHMAN

*Attesting Officer*  *Commissioner of Patents and Trademarks*